United States Patent
Kainoh et al.

(10) Patent No.: US 9,082,250 B2
(45) Date of Patent: Jul. 14, 2015

(54) AUTOMATIC DRUG DISPENSER

(75) Inventors: Naoshi Kainoh, Ehime (JP); Takumi Nishimura, Ehime (JP); Takanao Tanaka, Ehime (JP)

(73) Assignee: Panasonic Healthcare Co., Ltd. (JP)

( * ) Notice: Subject to any disclaimer, the term of this patent is extended or adjusted under 35 U.S.C. 154(b) by 207 days.

(21) Appl. No.: 13/696,092

(22) PCT Filed: Apr. 26, 2011

(86) PCT No.: PCT/JP2011/002450
§ 371 (c)(1),
(2), (4) Date: Nov. 5, 2012

(87) PCT Pub. No.: WO2011/138857
PCT Pub. Date: Nov. 10, 2011

(65) Prior Publication Data
US 2013/0054014 A1    Feb. 28, 2013

(30) Foreign Application Priority Data
May 7, 2010   (JP) .................................. 2010-107767

(51) Int. Cl.
G07F 17/00    (2006.01)
G06F 19/00    (2011.01)

(52) U.S. Cl.
CPC ........ *G07F 17/0092* (2013.01); *G06F 19/3462* (2013.01)

(58) Field of Classification Search
CPC .............. B42D 15/10; B42D 2035/04; B42D 2035/08; B42D 2035/40; B41J 2202/35; B41J 2/325; F25B 2500/13; F25D 23/006; G06F 19/3462; G06F 17/00; G07F 17/0092
USPC ........... 235/380, 492, 375, 494, 493; 400/103
See application file for complete search history.

(56) References Cited

U.S. PATENT DOCUMENTS

| 5,648,751 A | 7/1997 | Yuyama et al. |
| 5,988,858 A | 11/1999 | Yuyama et al. |
| 2002/0063698 A1* | 5/2002 | Koike et al. .................. 345/173 |
| 2008/0104830 A1 | 5/2008 | Yuyama et al. |
| 2011/0087368 A1* | 4/2011 | Shibata ......................... 700/231 |

FOREIGN PATENT DOCUMENTS

| JP | 08-131519 A | 5/1996 |
| JP | 09-051922 A | 2/1997 |
| JP | 2006-305099 A | 11/2006 |

(Continued)

OTHER PUBLICATIONS

CN Search Report for 201180022852.5, Sep. 6, 2013.

(Continued)

*Primary Examiner* — Sonji Johnson
(74) *Attorney, Agent, or Firm* — RatnerPrestia

(57) ABSTRACT

An automatic drug dispenser comprises: a non-filled tray unit for holding vacant trays, a drug feeding unit for feeding a stored drug to a tray in accordance with a pharmacist's instruction, a printer unit for outputting a printed sheet and feeding the printed sheet to the tray; a filled tray unit for holding the tray containing the drug and the printed sheet; and a tray-carrying unit. The tray is provided with an electronic card, in which patient's data is written, and the printer unit is provided, with an electronic card-writing unit for writing the patient's data to the electronic card.

6 Claims, 6 Drawing Sheets

(56) References Cited

FOREIGN PATENT DOCUMENTS

| | | |
|---|---|---|
| JP | 2008-119504 A | 5/2008 |
| JP | 2010-069173 A | 4/2010 |
| WO | WO 2010032411 A1 | 3/2010 |

OTHER PUBLICATIONS

International Search Report for Application No. PCT/JP2011/002450, dated Jun. 28, 2011, 3 pgs.

* cited by examiner

AUTOMATIC DRUG DISPENSER

TECHNICAL FIELD

The present invention relates to an automatic drug dispenser that dispenses drugs based on a pharmacist's instruction in clinics and the like.

BACKGROUND ART

An automatic drug dispenser refers to an apparatus that automatically dispenses drugs to a tray prepared for each of patients in accordance with prescriptions, injection prescriptions, or the like. In the automatic drug dispenser, a belt conveyor-shape carrying apparatus is used in order to dispense drugs to trays made to flow from upstream and carry the trays downstream. Here, an indicator for electronically indicating patient's information, such as the patient's name, on a side surface of each tray is proposed (refer to PTL 1 and 2). Thereby, it is possible to recognize to which patient drugs in each tray are prescribed, to recycle the indicator by electronically re-writing information, and to reduce waste.

RELATED ART DOCUMENTS

Patent Literatures

[Patent Literature 1] JP-A-8-131519
[Patent Literature 2] JP-A-9-51922

SUMMARY OF INVENTION

Problems to be Solved by the Invention

However, it takes a certain period of time to write patient's information in the indicator such that time required for drug dispensing increases. Particularly, in the case of medicine dispensing closely related with lives or bodies of patients, there is a strong demand for fast dispensing.

Alternatively, when patent's information is written in the indicator, there is a case in which writing of patient's information fails. In such a case, since the indicator displays nothing, it becomes unclear to which patient drugs in a tray are prescribed. As a result, dispensed drugs are disposed of, or efforts are taken to collect drugs dispensed to the automatic drug dispenser such that there is a problem in that economic efficiency or work efficiency deteriorates.

Alternatively, in a case in which patient's information is written in a non-contact manner, there is a concern that the patient's information may be leaked outside such that private information is leaked.

Therefore, an object of the invention is to provide an automatic drug dispenser which can significantly shorten a time required for drug dispensing.

Alternatively, an object of the invention is to provide an automatic drug dispenser in which patient's information and the like can be recognized even in a case in which writing errors and the like occur when patient's information is written in an indicator, such as an electronic card.

Alternatively, an object of the invention is to provide an automatic drug dispenser in which patient's information is not leaked outside.

Means for Solving the Problems

The inventions of the present application described below refer to the inventions specified in claims at the time of filing the application.

An automatic drug dispenser which is a first invention of the application is an automatic drug dispenser having a non-filled tray unit that holds vacant trays, a drug feeding unit that feeds a stored drug to the tray based on a pharmacist's instruction, a printer unit that prints a print and feeds the print to the tray, a filled tray unit that holds the tray to which the drug and the print have been fed, and a tray-carrying unit that carries the tray from the non-filled tray unit through the drug feeding unit and the printer unit to the filled tray unit, in which the tray is provided with an electronic card in which patient's information is written, and an electronic card-writing unit that writes the patient's information in the electronic card and is provided at the lower portion of the printer unit.

Here, the "electronic card" refers to a medium that holds patient's information, into which information, such as letters or data, is electrically, magnetically, and thermally written. In addition, the written information may be visible or invisible. The electronic card does not necessarily have a card shape, and may have an arbitrary shape, such as a block shape. In addition, any of non-contacting wireless means for which carrier waves, such as radio waves or infrared rays, are used and wired means for transmitting signals in a contact manner may be used as the writing unit. In addition, the writing unit may be means for transmitting heat in a contact manner.

In addition, the electronic card may be integrally formed with the tray, or detachably provided.

Furthermore, the "lower portion of the printer unit" may be located literally at the lower portion, and the electronic card may be provided with respect to any component. For example, the electronic card may be directly or indirectly provided on the tray-carrying unit, or may be provided on the printer unit side.

Meanwhile, the order of the drug feeding unit and the printer unit is arbitrary.

An automatic drug dispenser which is a second invention of the application is the automatic drug dispenser according to the first invention, in which the electronic card-writing unit detects whether or not the patient's information has been written in the electronic card, and, when the electronic card-writing unit has not written the patient's information in the electronic card, the printer unit prints the patient's information in the print and feeds the print to the tray.

An automatic drug dispenser which is a third invention of the application is the automatic drug dispenser according to the first invention including an electronic card-detecting unit that detects whether or not the electronic card is provided in the tray, in which, when the electronic card-detecting unit detects that the electronic card is not provided in the tray, the printer unit prints the patient's information in the print and feeds the print to the tray.

An automatic drug dispenser which is a fourth invention of the application is the automatic drug dispenser according to the third invention, in which the electronic card-detecting unit is the electronic card-writing unit.

An automatic drug dispenser which is a fifth invention of the application is the automatic drug dispenser according to the first invention, in which the electronic card-writing unit transmits the patient's information to the electronic card using directive carrier waves.

Here, "being directive" refers to a fact that the intensity of the carrier waves varies with direction.

In addition, the "carrier waves" refer to a transmitting medium that transmits the patient's information.

An automatic drug dispenser which is a sixth invention of the application is the automatic drug dispenser according to the fifth invention, in which the electronic card-writing unit is provided on the front surface side of the printer unit, and radiates the carrier waves toward the rear surface side of the printer unit.

Here, the "front surface side" refers to a side on which a user works in an ordinary state, or a side visible to a user in an ordinary state.

In addition, the "rear surface side" refers to the opposite location of the front surface side, and may be visible to a user or not.

An automatic drug dispenser which is a seventh invention of the application is the automatic drug dispenser according to the sixth invention, in which the rear surface of the printer unit is formed of a conductive member.

An automatic drug dispenser which is an eighth invention of the application is the automatic drug dispenser according to the seventh invention, in which a door is provided on the front surface of the printer unit, and an opening and closing-controlling unit for controlling opening and closing of the door is provided at the door.

Here, the "opening and closing-controlling unit" may use any of physical, electronic, and other methods as long as opening and closing of the door can be controlled.

An automatic drug dispenser which is a ninth invention of the application is the automatic drug dispenser according to the first invention, in which the tray-carrying unit is composed of a first tray-carrying unit provided below the drug feeding unit and a second tray-carrying unit which is a separate body from the first tray-carrying unit and provided below the printer unit, and the electronic card-writing unit is provided in the second tray-carrying unit.

Here, the "separate body" refers to not being physically integrally formed. That is, the "separate body" includes not only a body that is not in physical contact, but also a body that is in indirect contact through another member, for example, an anti-vibration member.

An automatic drug dispenser which is a tenth invention of the application is the automatic drug dispenser according to the ninth invention, in which an anti-vibration member that prevents transmission of vibrations is provided between the drug feeding unit and the printer unit.

Here, the "anti-vibration member" may use any of methods, such as absorption of vibrations or guidance to another portion, as long as transmission of vibrations is prevented. In addition, the "anti-vibration member" includes not only a member that completely prevents vibrations but also a member that partially prevents vibrations.

Advantage of the Invention

According to the first invention of the application, since the electronic card-writing unit is provided at the lower portion of the printer unit, writing on the electronic card can be performed in the printer unit while the print is waited for, and fast drug dispensing becomes possible compared to a case in which a step of writing for the electronic card is separately provided.

In addition, since the electronic card-writing unit is provided at the lower portion of the printer unit in which prescription, injection prescription, or patient's information called an application label is handled, devices that handle private information can be placed in the printer unit, a measure for preventing leakage of private information can be performed in the printer unit, and, furthermore, it becomes easy to clarify and manage a security zone.

In addition, since the electronic card-writing unit is provided at the lower portion of the printer unit, it is possible to prevent inconsistency between the contents in a print called prescription, injection prescription, an application label or the like and information written in the electronic card. That is, it is possible to place a tray in which information of the print, drug, and the electronic card is fully collected in one tray.

According to the second invention of the application, even in a case in which writing errors of patient's information occur on the electronic card, since the tray waits below the printer unit, it is possible to use the print instead of writing on the electronic card. That is, it is possible to determine to which patient dispensed drugs are prescribed, to reduce disposal of drugs or efforts for collecting drugs dispensed to the automatic drug dispenser, and to improve work efficiency.

According to the third invention of the application, even in a case in which the electronic card is not provided, similarly to the second invention, since the tray waits below the printer unit, it is possible to use the print instead of writing on the electronic card. That is, it is possible to determine to which patient dispensed drugs are prescribed, to reduce disposal of drugs or efforts for collecting drugs dispensed to the automatic drug dispenser, and to improve work efficiency.

According to the fourth invention of the application, the function of the electronic card-detecting unit can be realized using the electronic card-writing unit, and it is possible to make the configuration simple.

According to the fifth invention of the application, since patient's information is transmitted using directive carrier waves, diffusion of carrier waves can be suppressed, and leakage of private information can be prevented.

According to the sixth invention of the application, since the electronic card-writing unit radiates carrier waves from the front surface side to the rear surface side of the printer unit, it is not possible to detect private information from the front surface side of the printer unit at which an ordinary person works, and leakage of private information can be prevented.

According to the seventh invention of the application, since the rear surface of the printer unit is coated with the conductive member, carrier waves radiated from the electronic card-writing unit to the rear surface side hit the conductive member, and are directed to the ground level as it is, and therefore leakage of private information through the rear surface side can also be prevented.

According to the eighth invention of the application, since the door and the opening and closing-controlling unit are provided in the printer unit, it is possible to protect the security zone, that is, to prevent leakage of private information through direct access to a printed prescription or application label in the printer unit and an electronic card in which patient's information is written.

According to the ninth invention of the application, since the first tray-carrying unit and the second tray-carrying unit are separate bodies with respect to each other, it is difficult for vibrations due to movement of a picker of the drug feeding unit to be transmitted to the printer unit, and writing errors due to vibrations can be prevented.

According to the tenth invention of the application, since the drug feeding unit and the printer unit are connected to each other through the anti-vibration member, it is possible to prevent vibrations due to movement of the picker of the drug feeding unit from being transmitted to the printer unit, and writing errors due to vibrations can be prevented.

MODE FOR CARRYING OUT THE INVENTION (1. Overall Configuration of an Automatic Drug Dispenser)

Firstly, the overall configuration of an automatic drug dispenser of the present example will be described.

Figure 1:
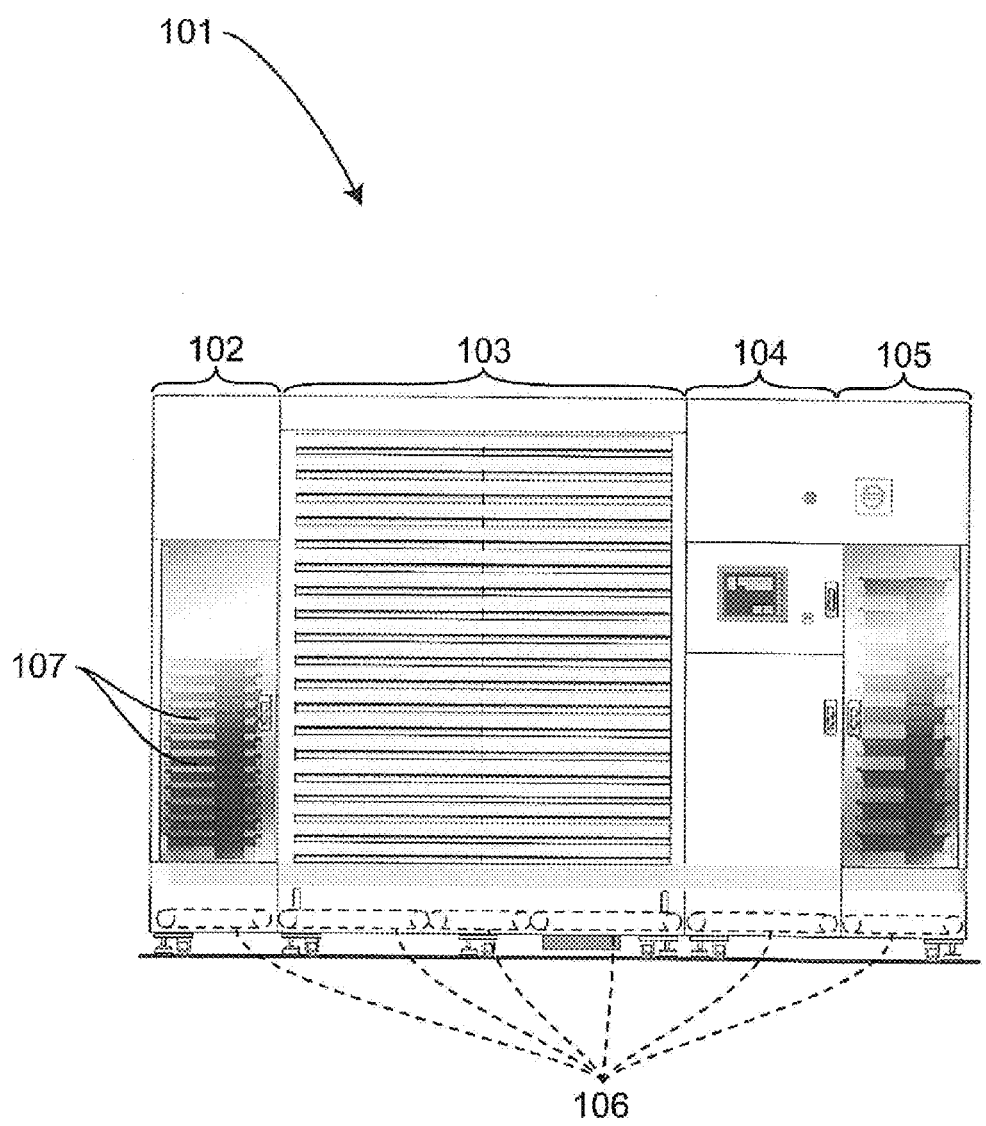
FIG. 1 is a front view of an automatic drug dispenser of the invention.

FIG. 1 is an appearance front view of an automatic drug dispenser 101 seen from the front surface side. The automatic drug dispenser 101 is composed of a non-filled tray unit 102, a drug feeding unit 103, a printer unit 104, a filled tray unit 105, and a tray-carrying unit 106 for combining the above.

The non-filled tray unit 102 accumulates and holds vacant trays 107 for placing a variety of drugs, and supplies the vacant trays to the tray-carrying unit 106 provided at the lower portion. In the example, the non-filled tray unit 102 has a door formed of transparent plastic, glass, or the like at the front surface so that the inventory of the trays 107 can be confirmed, but the covering is not necessarily required, and the non-filled tray unit may accumulate and holds the trays 107 in a manner in which the trays are exposed.

The drug feeding unit 103 sorts and stores a variety of drugs, references prescription data and the like, and feeds and places drugs necessary for each patient in the vacant tray 107 moved from the non-filled tray unit 102 through the tray-carrying unit 106 using a picker based on a pharmacist's instruction from a control apparatus, such as a computer, not shown. Drugs are subjects of prescription, and examples thereof include injection drugs, medicinal drops, internal medicines, adhesive medicines, suppositories, and the like. In addition, packages of drugs are typically an ampoule or a plastic bottle for injection drugs, an infusion solution pack for medicinal drops, a small bottle, an SP package, a PTP package, or the like for internal tablets, powdered drugs, and the like.

The printer unit 104 has a printer that prints prescriptions, injection prescriptions, and application labels of a variety of medicines in which the contents of medicine prescriptions are written based on prescription data, and feeds and places printed prescriptions and the like or application labels in the tray 107 moved from the drug feeding unit 103 through the tray-carrying unit 106. In the example, the printer unit 104 is covered with a nontransparent metal or plastic door on the front surface in order to prevent intrusion of dust or foreign substances from outside, and the door can be opened and closed. Information displayed on a print printed using the printer or an electronic card described below describes and displays private information, and has high confidentiality. Therefore, the printer unit 104 is desirably managed as an area in which private information is collected and as a security zone. Therefore, in order to prevent leakage of private information, the opening and closing of the door is desirably controlled by providing an opening and closing-controlling unit composed of a physical means composed of a variety of keys or an electronic means composed of an ID card and a personal authentication means that performs fingerprint authentication, iris scanning, or the like. In addition, the rear surface of the printer unit 104 of the example is formed of a steel sheet which is a conductive member. Desirably, the rear surface may be grounded using an earth. Meanwhile, it is not necessary to form the entire surface of the rear surface using a conductive material, and the conductive material simply needs to be formed so as to cover at least an area hit by carrier waves which will be described below.

In addition, an electronic card-writing unit described below is provided at the lower portion of the printer unit 104. Meanwhile, the drug feeding unit 103 and the printer unit 104 may be disposed reversely.

Figure 6:
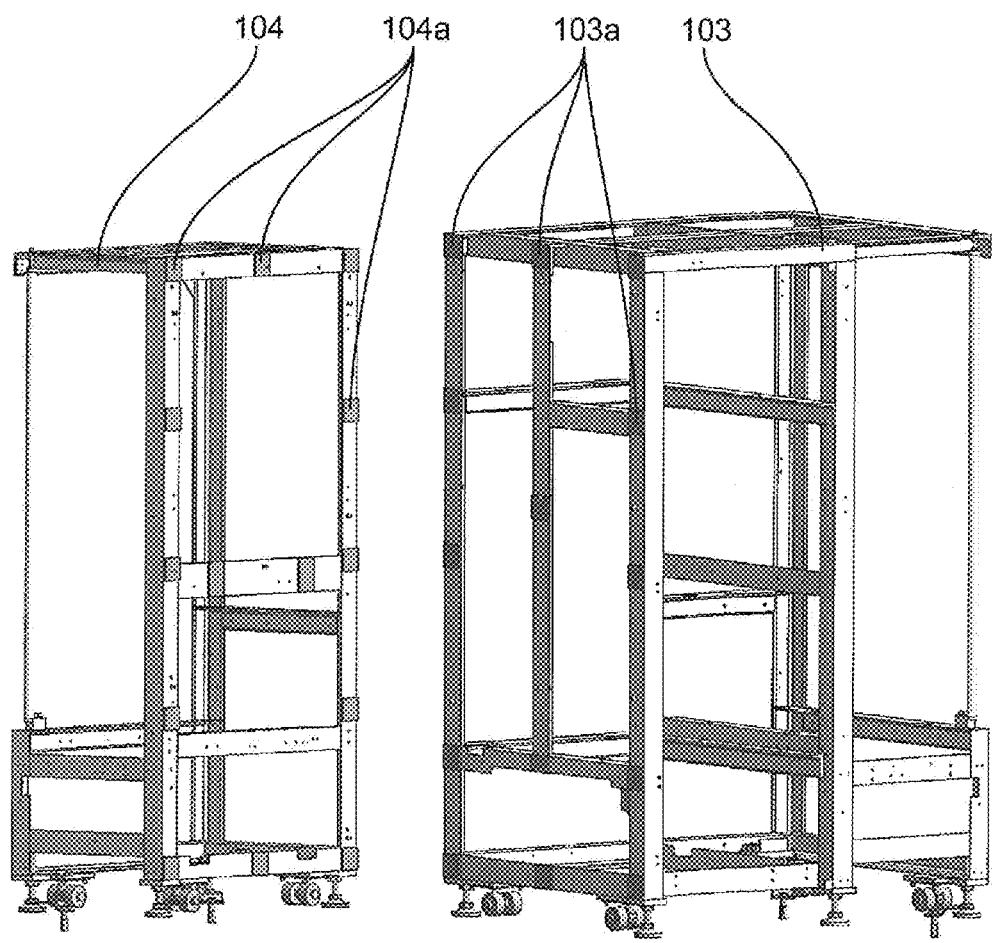
FIG. 6 is a perspective view of a frame that composes a printer unit and a drug feeding unit of the same dispenser.

Meanwhile, in the example, the drug feeding unit 103 and the printer unit 104 are configured as separate bodies; however, as a more desirable form, an anti-vibration measure as shown in FIG. 6 is performed particularly to prevent vibrations generated due to operation of the picker of the drug feeding unit 103 from being transmitted to the printer unit 104.

That is, in FIG. 6, anti-vibration members 103a are provided at appropriate intervals on a frame surface of the drug feeding unit 103 which comes into contact with the printer unit 104, and anti-vibration members 104a are provided at appropriate intervals on a frame surface of the printer unit 104 which comes into contact with the drug feeding unit 103.

The anti-vibration members 103a and 104a simply need to be able to prevent transmission of vibrations, and for example, low repulsion urethane sheets or foamable high molecular materials can be used.

Meanwhile, the anti-vibration members 103a and 104a are provided at both the drug feeding unit 103 and the printer unit 104 in the example, but may be provided at any one of them. That is, the anti-vibration members simply need to be provided at least between the drug feeding unit 103 and the printer unit 104.

The filled tray unit 105 receives, accumulates, and holds the trays 107 moved from the printer unit 104 using the tray-carrying unit 106. At this point in time, a variety of drugs, prescriptions, injection prescriptions, and application labels are placed in the trays 107. Similarly to the non-filled tray unit 102, the filled-tray unit 105 also has a door formed of transparent plastic, glass, or the like at the front surface so that the filled trays can be confirmed. In addition, the above configuration can prevent the trays 107 in which medicines are places from collapsing such that the medicines are destroyed. However, functionally, the covering is not necessarily required, and the filled tray unit may accumulate and hold the trays 107 in a manner in which the trays are exposed. In addition, the trays 107 accumulated in the filled tray unit 105 are shuffled to a cart or the like, and transported to doctors or patients by nurses, pharmacists, and the like.

Meanwhile, in a case in which the security zone matters, the entire surface of the filled tray unit 105 may be made to be nontransparent, and the same opening and closing-controlling unit as for the printer unit 104 may be provided so as to control opening and closing of the door.

The tray-carrying unit 106 connects the filled tray unit 105 from the non-filled tray unit 102 through the drug feeding unit 103 and the printer unit 104 using means, such as a belt conveyor. The tray-carrying unit 106 may integrate the respective units in a straddle form; however, according to the example, since vibrations of the drug feeding unit 103 are prevented from being transmitted to the electronic card-writing unit described below which is provided at the lower portion of the printer unit 104, as a more preferable form, the tray-carrying unit is independently provided at the lower portion of each of the units. Operations of the tray-carrying unit 106 are receiving the vacant trays 107 from the non-filled tray unit 102, receiving medicines from the drug feeding unit 103 and prescriptions and the like or application labels from the printer unit 104 on the trays 107, and passing the trays 107 in which the medicines and the prescriptions are placed to the filled tray unit 105. As such, provision of the tray-carrying unit 106 in a series can perform tray supply, drug feeding, print feeding, and tray dispensing in parallel at the same time at the respective units, and faster drug dispensing can be realized. The detailed configuration and actions of the tray-carrying unit 106 will be described below.

(2. Tray-Carrying Unit)

Figure 2:
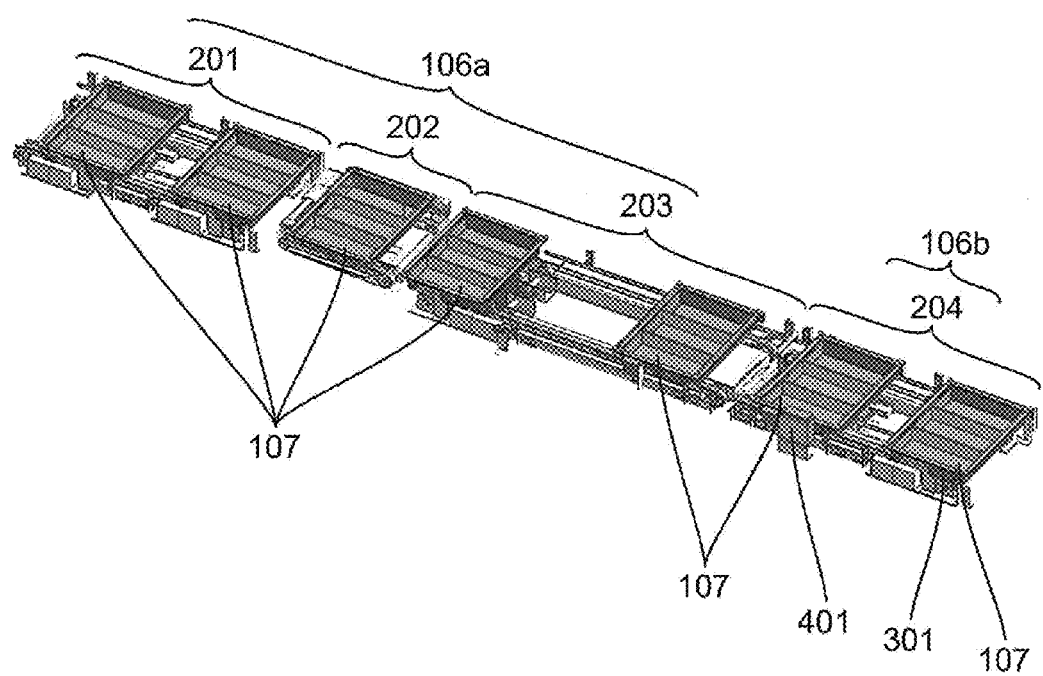
FIG. 2 is an appearance perspective view of a tray-carrying unit in the same dispenser.

The configuration of the tray-carrying unit 106 will be described using FIG. 2. FIG. 2 is an appearance perspective view of the tray-carrying unit 106 at the lower portion of the drug feeding unit 103 and at the lower portion of the printer unit 104 which is seen from the front surface side.

In the tray-carrying unit 106, a first tray-carrying unit 106a located at the lower portion of the drug feeding unit 103 is composed of a combination of a plurality of belt conveyors. That is, the first tray-carrying unit 106a is composed of a first conveyor 201, a second conveyor 202, and a third conveyor 203.

The first conveyor 201 has a roller, a belt, and a motor for driving the roller, and receives instructions from a control apparatus, such as a computer, not shown, so as to drive the motor, thereby carrying the trays 107. In addition, the first conveyor 201 is located on the upstream side of the drug feeding unit 103, and plays roles of receiving the trays 107 flowed from the non-filled tray unit 102 side and passing the trays to the second conveyor 202. Meanwhile, when a tray 107 stays in the second conveyor 202, the other tray may be controlled to wait on the first conveyor 201.

The second conveyor 202 is located between the first conveyor 201 and the third conveyor 203, and plays roles of passing the tray to the third conveyor 203 and making swirling actions for itself so as to change the orientation of the trays 107. In addition, drugs are fed into the tray 107 using a feeding means, such as a picker, that grips necessary drugs at this location. Drugs can be fed into a desired location in the tray 107 in synchronization with such feeding and the swirling action of the second conveyor 202.

Similarly to the first conveyor 201, the third conveyor 203 also has a roller, a belt, and a motor for driving the roller, and receives instructions from a control apparatus, such as a computer, not shown, so as to drive the motor, thereby carrying the trays 107. In addition, the third conveyor 203 is located on the downstream side of the drug feeding unit 103, and plays a role of passing the tray 107 filled with drugs to a conveyor 204 provided in the printer unit 104.

In the tray-carrying unit 106, the second tray-carrying unit 106b located at the lower portion of the printer unit 104 has one conveyor 204.

The conveyor 204 also has a roller, a belt, and a motor for driving the roller, and receives instructions from a control apparatus, such as a computer, not shown, so as to drive the motor, thereby carrying the trays. In addition, the conveyor 204 plays roles of receiving the trays 107 flowed from the third conveyor 203 in the tray-carrying unit 106a, waiting for prescriptions, injection prescriptions, and prints, such as application labels of a variety of medicines which are printed using the printer unit 104, waiting for completion of writing on an electronic card described below and passing the tray to the tray-carrying unit 106 provided below the filled tray unit 105 after that waiting.

Meanwhile, the first tray-carrying unit 106a and the second tray-carrying unit 106b may be integrated. Even in the form of an integrated body, a time required for drug dispensing can be shortened, and a measure for preventing leakage of private information can be applied to the printer unit 104.

However, like the example, when the first tray-carrying unit 106a located below the drug feeding unit 103 and the second tray-carrying unit 106b located below the printer unit 104 are provided as separate conveyors, furthermore, it is possible to prevent vibrations generated due to movement of the picker of the drug feeding unit 103 or vibrations of the first conveyor 201, the second conveyor 202, and the third conveyor 203 in the first tray-carrying unit 106a from being transmitted to the second tray-carrying unit 106b.

(3. Electronic Card and Electronic Card-Writing Unit)

In FIG. 2, an electronic card-writing unit 401 is provided at the flank of the conveyor 204 in the second tray-carrying unit 106b. The electronic card-writing unit 401 is provided on the front surface side of the printer unit 104 in the example. Therefore, the electronic card-writing unit 401 radiates carrier waves toward the rear surface side of the printer unit 104. Specifically, writing is performed by transmitting and radiating carrier waves containing patient's information, such as dates, patient's name, ward, patient's room, and patient ID, to an electronic card 301 provided at the side surface of the tray 107 flowed on the conveyor 204, and the patient's information is displayed on the display means on the electronic card 301. In addition, according to necessity, information, such as the contents of prescriptions and the kinds of prescribed drugs, is written at the same time.

Meanwhile, in the example, the electronic card-writing unit 401 is provided in the second tray-carrying unit 106b as a desirable example, and the electronic card-writing unit may be not only directly provided in the second tray-carrying unit 106b, but also indirectly provided through a certain member. Alternatively, the electronic card-writing unit may be fixed to the printer unit 104 side. In summary, the electronic card-writing unit may be provided at the lower portion of the printer unit 104.

Next, the configurations and operations of the electronic card and the electronic card-writing unit will be described using FIGS. 3 and 4.

Figure 3:
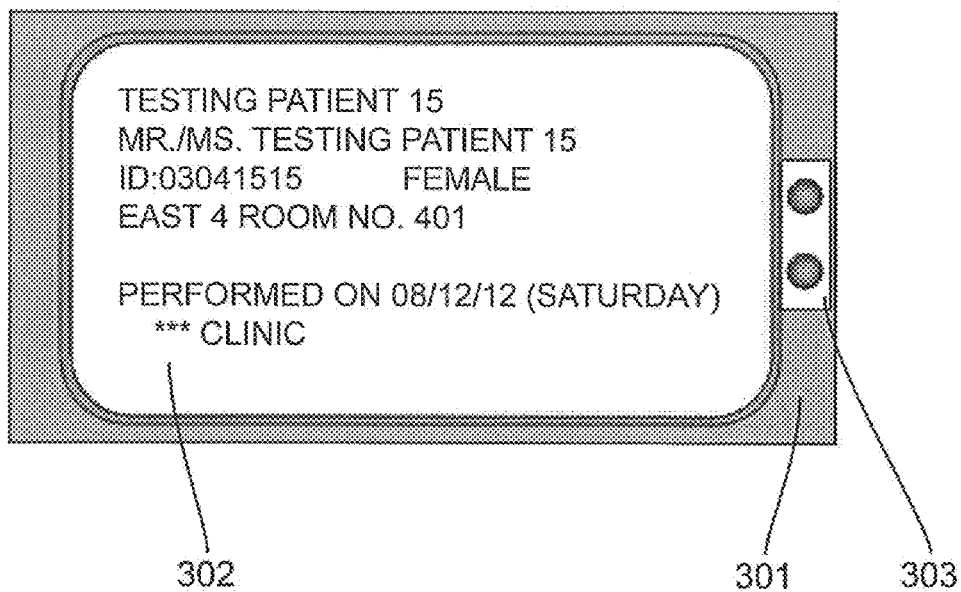
FIG. 3 is a front view of an electronic card provided in a tray used in the same dispenser.

In FIG. 3, 301 indicates an electronic card which is held and maintained in a patient card holder provided on the side surface of the tray 107. The electronic card 301 electronically records patient's information. In the electronic card 301, an indicator 302 composed of a display means, such as a liquid crystal panel, and a transmitting and receiving portion 303 composed of an IrDA are provided.

Patient's information, such as prescription date of drugs, patient's name, ward, patient's room, and patient ID, is written in the electronic card 301, and displayed on the indicator 302 composed of a liquid crystal panel.

Meanwhile, the electronic card may directly change display using a magnetic means or a thermal means.

In addition, according to necessity, a recording means may be provided in the electronic card 301 so as to record the above patient's information or other patient's information in the recording means. For example, the electronic card may be operated in the following manner: prescription history of drugs, hospital history, and the like of the past are recorded, and nurses scan and confirm the information using a portable terminal at the time of drug prescription or medication.

Furthermore, in the invention, the electronic card may be a type in which the indicator 302 is not provided, and information is only written in the recording means. A scanning apparatus for scanning information from the recording means may be used so that the information is displayed only to authorized persons.

Figure 4:
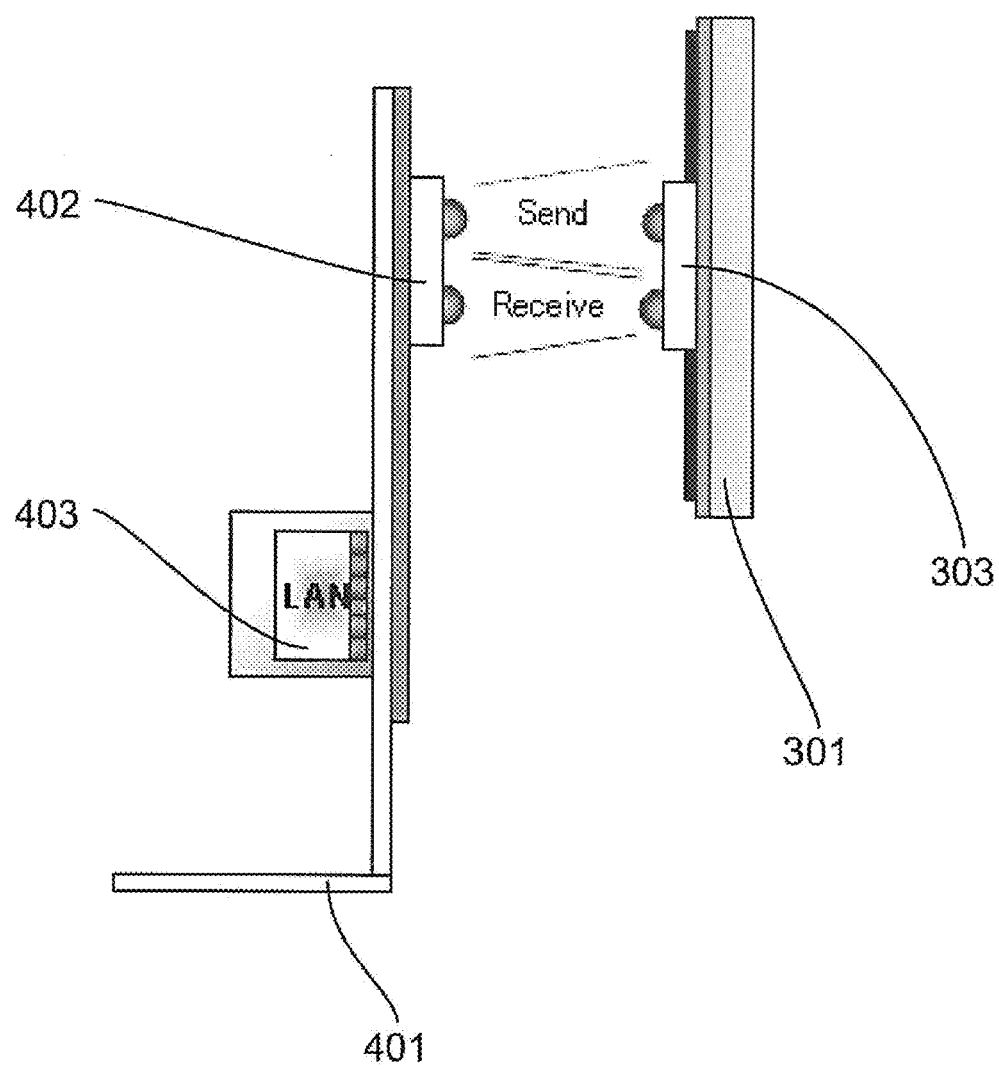
FIG. 4 is a configuration view of an electronic card-writing unit in the same dispenser.

In FIG. 4, 401 indicates an electronic card-writing unit which writes patient's information in the electronic card 301. A transmitting and receiving portion 402 composed of an IrDA and a communicating means 403 of patient's information or control signals are provided in the electronic card-writing unit 401.

The operation of the electronic card-writing unit 401 will be described. When the electronic card 301 held on the side surface of the tray 107 is detected, the electronic card-writing unit 401 transmits patient's information, such as dates, patient's name, ward, patient's room, patient's ID, furthermore, the contents of prescriptions or the kinds of prescribed drugs which has been transmitted from a computer, not shown, through the communicating means 403 toward the electronic card 301 from the transmitting and receiving portion 402. In contrast, the transmitting and receiving portion 303 in the electronic card 301 receives such information, stores the information, such as dates, patient's name, ward, patient's room, and patient's ID, in the recording means, such as a semiconductor memory, provided inside, and performs display on the indicator 302. In addition, other information is stored in the recording means, such as a semiconductor memory. In addition, a confirming signal through which receiving of the information is confirmed is transmitted from the transmitting and receiving portion 303 of the electronic card 301. When the transmitting and receiving portion 402 of the electronic card-writing unit 401 receives the signal, writing on the electronic card 301 is detected to have ended.

Meanwhile, in the example, the electronic card-writing unit 401 uses an IrDA that writes information in a non-contact manner to the electronic card 301, but may use means that writes information in a contact manner. In the case of means that write in a contact manner, the risk of leakage of patient's information can be decreased. In addition, regarding vibrations, the risk of generation of writing errors also decreases.

In addition, other non-contact means include means using specific low power wireless. In addition, use of an RFID is also considered.

In the example, since an IrDA, that is, infrared rays are used as the carrier waves, the communicable distance is short, and the risk of leakage of patient's information is small. In addition, since infrared rays are directive and have a narrow radiation range, similarly, the risk of leakage of patient's information is small.

Even in a case in which a small risk of leakage of patient's information is realized using a specific small power wireless or an RFID, a desirable design is that the directive properties of carrier waves be adjusted so that radio waves reach only a necessary range (angle or distance).

Furthermore, in the example, since the electronic card-writing unit 401 is provided on the front surface side of the printer unit 104, carrier waves are radiated toward the rear surface side. Therefore, it is not possible to receive carrier waves on the front surface side of the printer unit 104 at which an operator usually works, and the risk of leakage of patient's information further decreases. Additionally, the rear surface of the printer unit 104 is composed of a conductive steel sheet, carrier waves that have hit the steel sheet are directed to the ground level, and therefore carrier waves, such as infrared rays or radio waves, do not leak outside the printer unit 104 due to a screening effect, and the risk of leakage of patient's information decreases.

(4. Actions)

Figure 5:
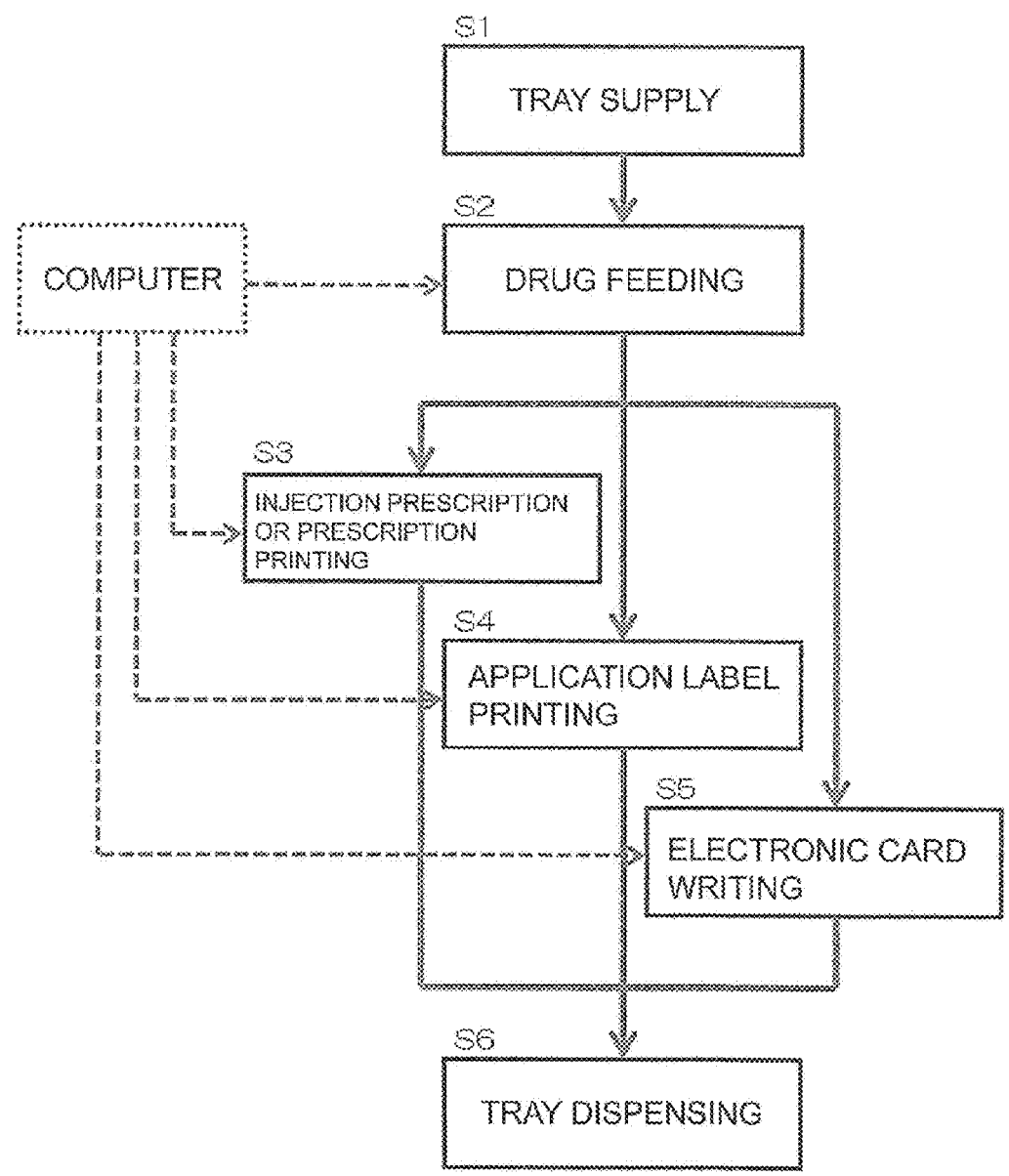
FIG. 5 is an explanatory view showing actions of the same dispenser.

The actions of the automatic drug dispenser 101 having the above configuration, particularly, the actions below the printer unit 104 will be described using FIG. 5. Firstly, the vacant tray 107 holding the electronic card 301 on the side surface is supplied to the drug feeding unit 103 from the non-filled tray unit 102 (S1).

In addition, the drug feeding unit 103 which has received a pharmacist's instruction from a computer based on a prescription controls the tray-carrying unit 106a and the picker, not shown, so as to feed predetermined drugs into the vacant tray 107 and dispense the drugs (S2).

The tray-carrying unit 106b of the printer unit 104 which has received the tray 107 to which drugs have been dispensed from the tray-carrying unit 106a stops carrying of the tray 107 at a predetermined location of the tray-carrying unit 106b. In addition, the printer unit 104 receives a printing instruction of prescriptions or injection prescriptions from the computer so as to print prescriptions or injection prescriptions, receives a printing instruction of an application label so as to print the application label, and feeds and places the prints of prescriptions or injection prescriptions, the application label, and the like on the tray 107 (S3, S4).

Desirably, at the same time as the above or before or after this phase, the electronic card-writing unit 401 receives an electronic card-writing instruction from the computer, writes patient's information, such as dates, patient's name, ward, patient's room, and patient's ID, in the electronic card 301 provided in the tray 107, and displays on the display means 302 (S5).

When the above steps are over, the tray-carrying unit 106b dispenses the tray 107 which has completed dispensing drugs or necessary prints, and writing on the electronic card 301 to the filled tray unit 105 (S6).

According to the above actions, writing on the electronic card 301 can be performed while printing of the print is waited for in the printer unit 104, and the dispensing time of drugs can be shortened compared to an automatic drug dispenser in which writing on the electronic card 301 is performed on an independent area on a conveyor.

In addition, when the printer unit 104 is disposed after the drug feeding unit 103, since drugs have already been dispensed on the tray 107, dispensing or displaying of the print or the electronic card 301 can be performed after dispensing of drugs has been confirmed, and it is easy to match drugs on the tray 107 and information displayed using the print or the electronic card 301, whereby accurate dispensing of drugs can be guaranteed.

(5. Actions in Case of Failure of Writing)

Writing on the electronic card 301 is performed in S5; however, in a case in which writing fails, a disadvantage of dispensing a tray having no display or information in the electronic card 301 occurs. Even in this case, since the electronic card-writing unit 401 is present at the lower portion of the printer unit 104, a printer in the printer unit 104 can output patient's information alternatively.

Therefore, when writing on the electronic card 301 fails in S5, that is, in a case in which a confirming signal from the electronic card 301 is a signal that indicates failure of writing, or a confirming signal is not transmitted within a predetermined time so as not to be detected in the transmitting and receiving portion 402 of the electronic card-wiring unit 401, it is also possible to make a printing instruction to the printer unit 104 instead of writing on the electronic card 301, and to feed and place a print on which dates, patient's name, ward, patient's room, and patient's ID are printed. By doing so, there is no case in which the tray 107 having an unclear prescription target is dispensed, it is not necessary to dispose of drugs due to unclear prescription target, or an effort to collect drugs to the drug feeding unit 103 can be saved.

As described above, whether or not writing is possible can be detected using the contents of a confirming signal from the electronic card 301 or the presence of a confirming signal. Examples of a case in which writing on the electronic card 301 is not possible include a case in which the electronic card 301 is not mounted in a holder in the tray 107, a case in which the orientation of the tray 107 is opposite, a case in which the electronic card 301 has a poor quality, a case in which an electronic card-writing operation ends in failure due to transmitting and receiving errors or the like, and the like.

In addition, there is a case in which writing on the electronic card 301 is not possible due to the poor quality or the like of the electronic card-writing unit 401. Failure of writing on the electronic card 301 can be detected by detecting the contents or presence of signals from the communicating means 403 using a control means, such as a computer, not shown.

Alternatively, in S5, detection of the presence of the electronic card 301 may be performed before writing on the electronic card 301. The detection is performed using an electronic card-detecting unit for directly or indirectly detecting the presence of the electronic card 301. Examples of the former case include means which is composed of a light-emitting element and a light-receiving element, and has a disposition in which the detection results at the light-receiving element vary by the presence of the electronic card. In addition, examples of the latter case include use of a bar code reader. That is, it is possible to have a bar code on a side surface of the tray 107 and provide a bar code reader in the tray-carrying unit 106b, thereby indirectly detecting the presence of the electronic card 301 using the orientation of the tray.

Since the electronic card-writing unit 401 also has the function of the electronic card-detecting unit, the electronic card-writing unit 401 may be used as the electronic card-detecting unit.

In addition, detection of the presence of the electronic card 301 may be performed not only before writing on the electronic card 301 but also after writing or at the same time as writing.

Furthermore, when the electronic card-writing unit 401 detects absence of the electronic card 301, it is also possible to detect whether or not the orientation of the tray 107 is opposite, if the orientation of the tray 107 is opposite, to rotate reversely the conveyor 204 in the tray-carrying unit 106b and the third conveyor 203 and the second conveyor 202, to return the tray 107 to the second conveyor 202, and to rotate the tray 107 on the second conveyor 202, thereby correcting the orientation of the tray 107 to a correct orientation.

Meanwhile, in all cases in which writing on the electronic card 301 is not possible, it is not necessary to print patient's information and the like from the printer unit 104 on a print so as to feed to the tray 107.

For example, it is possible to not print patient's information when writing fails at the first attempt and to print the patient's information when writing fails at the second attempt.

Alternatively, in a case in which the electronic card 301 is repeatedly used, it is possible to print patient's information when writing fails at the first attempt, and, when writing fails at the second attempt, to stop the system during determination of malfunction of the electronic card 301 and prompt replacement of the electronic card 301.

Additionally, in the case of specific conditions, patient's information may not be printed.

That is, a case in which patient's information is printed for a reason of failure of writing on the electronic card 301 belongs to the invention.

INDUSTRIAL APPLICABILITY

The invention can be used not only in an automatic drug dispenser in clinics but also in an apparatus that sorts and holds a variety of drugs in trays in accordance with predetermined information.

DESCRIPTION OF REFERENCE NUMERALS AND SIGNS

101 AUTOMATIC DRUG DISPENSER
102 NON-FILLED TRAY UNIT
103 DRUG FEEDING UNIT
103a ANTI-VIBRATION MEMBER
104 PRINTER UNIT
104a ANTI-VIBRATION MEMBER
105 FILLED TRAY UNIT
106 TRAY-CARRYING UNIT
107 TRAY
201 FIRST CONVEYOR
202 SECOND CONVEYOR
203 THIRD CONVEYOR
204 CONVEYOR
301 ELECTRONIC CARD
302 INDICATOR
303 TRANSMITTING AND RECEIVING PORTION
401 ELECTRONIC CARD-WRITING UNIT
402 TRANSMITTING AND RECEIVING PORTION
403 COMMUNICATING MEANS

The invention claimed is:

1. An automatic drug dispenser comprising:
a non-filled tray unit that holds vacant trays;
a drug feeding unit that feeds a stored drug to the tray based on a pharmacist's instruction;
a printer unit that outputs a printed sheet and feeds the printed sheet to the tray;
a filled tray unit that holds the tray to which the drug and the printed sheet have been fed; and
a tray-carrying unit that carries the tray from the non-filled tray unit through the drug feeding unit and the printer unit to the filled tray unit,
wherein the tray is provided with an electronic card in which patient's information is written, after feeding the drug to the tray and before dispensing the drug to the filled tray unit, and at the same time or almost simultaneously feeding the printed sheet to the tray,
wherein an electronic card-writing unit that writes the patient's information in the electronic card is provided at the lower portion of the printer unit, and
that prescription date of drugs, patient's name, ward, patient's room and patient ID in the patient's information are written in the electronic card by the electronic card-writing unit, and displayed on an indicator, and
the contents of prescriptions or the kinds of prescribed drugs in the patient's information are recorded by a recording means provided on the electronic card.

2. The automatic drug dispenser according to claim 1,
wherein the electronic card-writing unit detects whether or not the patient's information has been written in the electronic card, and
when the electronic card-writing unit has not written the patient's information in the electronic card, the printer unit prints the patient's information in the printed sheet and feeds the printed sheet to the tray.

3. The automatic drug dispenser according to claim 1, comprising,
- an electronic card-detecting unit that detects whether or not the electronic card is provided in the tray,
- wherein, when the electronic card-detecting unit detects that the electronic card is not provided in the tray, the printer unit prints the patient's information in the printed sheet and feeds the printed sheet to the tray.

4. The automatic drug dispenser according to claim 3,
- wherein the electronic card-detecting unit is the electronic card-writing unit, unit.

5. The automatic drug dispenser according to claim 1,
- wherein the tray-carrying unit includes a first tray-carrying unit provided below the drug feeding unit and a second tray-carrying unit which is a separate body from the first tray-carrying unit and is provided below the printer unit, and
- the electronic card-writing unit is provided in the second tray-carrying unit.

6. The automatic drug dispenser according to claim 5,
- wherein an anti-vibration member that prevents transmission of vibrations is provided between the drug feeding unit and the printer unit.

* * * * *